US010388249B2

(12) United States Patent
Beckmann

(10) Patent No.: US 10,388,249 B2
(45) Date of Patent: *Aug. 20, 2019

(54) MULTIFUNCTIONAL OPERATING DEVICE FOR DISPLAYING A REMOTE APPLICATION IN A VEHICLE

(71) Applicant: VOLKSWAGEN AG, Wolfsburg (DE)

(72) Inventor: Mark Beckmann, Braunschweig (DE)

(73) Assignee: VOLKSWAGEN AG, Wolfsburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/849,366

(22) Filed: Dec. 20, 2017

(65) Prior Publication Data
US 2018/0114503 A1 Apr. 26, 2018

Related U.S. Application Data

(63) Continuation of application No. 14/002,230, filed as application No. PCT/EP2012/000973 on Mar. 5, 2012, now Pat. No. 9,881,583.

(30) Foreign Application Priority Data

Mar. 12, 2011 (DE) .......... 10 2011 013 757
Sep. 3, 2011 (DE) .......... 10 2011 112 445

(51) Int. Cl.
B60K 35/00 (2006.01)
G09G 5/00 (2006.01)
(Continued)

(52) U.S. Cl.
CPC .............. G09G 5/006 (2013.01); A61B 5/18 (2013.01); B60K 35/00 (2013.01); B60K 37/06 (2013.01);
(Continued)

(58) Field of Classification Search
CPC ........ B60K 2350/352; B60K 2350/355; B60K 2350/357

See application file for complete search history.

(56) References Cited

U.S. PATENT DOCUMENTS 6,262,657 B1 7/2001 Okuda et al.
7,216,022 B2 5/2007 Kynast et al.
(Continued)

FOREIGN PATENT DOCUMENTS

DE 199 41 963 A1 4/2000
DE 100 39 795 A1 3/2002
(Continued)

OTHER PUBLICATIONS

Bose, Raja et al., "Terminal Mode—Transforming Mobile Devices into Automotive Application Platforms," Proceedings of the 2nd International Conference on Automotive User Interfaces and Interactive Vehicular Applications (AutomotiveUI 2010), Nov. 2010, pp. 148-155.

(Continued)

Primary Examiner — Ryan McCulley
(74) Attorney, Agent, or Firm — Hunton Andrews Kurth LLP

(57) ABSTRACT

In a method and devices, data for the display of an application on a screen is provided. In addition, information with regard to a degree of distraction of the application, e.g., information regarding user-interface elements, and/or information regarding a degree of distraction of a driver of a vehicle (110) is provided. As a function of this information and a driving situation of the vehicle, it is decided whether the application will be displayed on the screen.

24 Claims, 3 Drawing Sheets

(51) Int. Cl.
*B60K 37/06* (2006.01)
*G01C 21/36* (2006.01)
*A61B 5/18* (2006.01)

(52) U.S. Cl.
CPC ........... *G01C 21/36* (2013.01); *G01C 21/367* (2013.01); *B60K 2350/1096* (2013.01); *B60K 2350/352* (2013.01); *B60K 2350/962* (2013.01); *B60K 2350/965* (2013.01)

(56) References Cited

U.S. PATENT DOCUMENTS

| | | |
|---|---|---|
| 2006/0058963 A1 | 3/2006 | Smith et al. |
| 2006/0190822 A1 | 8/2006 | Basson et al. |
| 2009/0240464 A1 | 9/2009 | Dietz et al. |
| 2010/0293462 A1 | 11/2010 | Bull et al. |
| 2011/0111724 A1 | 5/2011 | Baptiste |
| 2011/0214162 A1 | 9/2011 | Brakensiek et al. |

FOREIGN PATENT DOCUMENTS

| | | |
|---|---|---|
| DE | 102 28 703 A1 | 1/2004 |
| DE | 10 2006 050 017 A1 | 4/2008 |
| EP | 0 701 926 A2 | 3/1996 |
| EP | 1 870 673 A2 | 12/2007 |
| WO | 2009/143903 A1 | 12/2009 |

OTHER PUBLICATIONS

International Search Report dated Jul. 23, 2012, in corresponding International Application No. PCT/EP2012/000973.

MULTIFUNCTIONAL OPERATING DEVICE FOR DISPLAYING A REMOTE APPLICATION IN A VEHICLE

CROSS-REFERENCE TO RELATED APPLICATIONS

The present application is a continuation of U.S. patent application Ser. No. 14/002,230, filed on Aug. 29, 2013, which is a national phase of PCT International Patent Application No. PCT/EP2012/000973, filed on Mar. 5, 2012, which claims priority to German Patent Application No. 10 2011 112 445.8, filed on Sep. 3, 2011, and to German Patent Application No. 10 2011 013 757.2, filed on Mar. 12, 2011, each of which is expressly incorporated herein in its entirety by reference thereto.

FIELD OF THE INVENTION

The present patent application relates to a multifunctional operating device as well as a method for operating such a multifunctional operating device in vehicles, for example, in motor vehicles, and vehicles equipped accordingly.

BACKGROUND INFORMATION

Multifunctional elements and multifunctional operating devices for motor vehicles are known in various form. Using such multifunctional operating devices, different units in a motor vehicle, for example, radio, CD player, navigation system, on-board computer or telephone system, are able to be controlled by a single operating device. Multifunctional operating devices are described, for instance, in European Published Patent Application No. 0 701 926, which describes a multifunctional operating device in which a screen as well as one or more keypads are used.

A further multifunctional operating device is described in German Published Patent Application No. 199 41 963, in which likewise a screen as well as control buttons located on the edge of the screen are used.

A further possibility for operative control, which is being used increasingly in the case of electronic devices, is operative control with the aid of touch-sensitive screens, referred to as touchscreens. Here, operating elements such as push buttons or slide controls are able to be displayed directly on the touch-sensitive screen and operated by touching this screen. For example, the use of such touchscreens is widespread in mobile phones. In this manner, various operator interfaces for operating different functions and devices may be displayed flexibly on the screen.

However, in using a multifunctional operating device having a touch-sensitive screen for displaying different operator interfaces, the problem may arise that for many applications, the operator interface is so complex that, for example, the operative control could distract a driver of a motor vehicle to such an extent that safe driving of the vehicle would no longer be ensured.

In particular, such a distraction of the driver may occur if the multifunctional operating device is used as client and the application is running on a server; in many cases, the server may also be a mobile telephone, so that in such a case, an application of the mobile telephone is displayed on the multifunctional operating device. As a rule, such applications on mobile telephones are not optimized for use in a vehicle and may therefore lead especially easily to a distraction.

Regarding this, it is described in German Published Patent Application No. 100 39 795 to generally monitor the attentiveness of a driver and to output a warning, if necessary. U.S. Pat. No. 6,262,657 describes warning a driver if telephoning using a mobile telephone is leading to an unstable driving situation.

SUMMARY

Example embodiments of the present invention provide operating devices and corresponding methods, using which, the risk of a driver in a motor vehicle becoming distracted is reduced.

A method according to an example embodiment of the present invention includes: providing data for the display of an application on a screen, providing information with regard to a degree of distraction, and displaying the application on the screen as a function of the information regarding the degree of distraction and a driving situation of a vehicle.

The display of the application as a function of the information with regard to the degree of distraction and a driving situation of the vehicle may include a decision as to whether the application is displayed on the screen.

The provision of information with regard to a degree of distraction may include providing information regarding a degree of distraction of or caused by the application, that is, the provision of information which is characteristic for how much the application is capable of distracting a driver or other operator of the application.

In this manner, it is possible to decide in a flexible manner whether and how the application may be displayed on the screen in a specific driving situation, without unacceptably impairing driving safety.

In particular, the provision of information regarding the degree of distraction may include providing information with respect to user-interface elements of the application to be displayed on the screen. In this context, for example, a multitude of user-interface elements, small user-interface elements and/or user-interface elements complicated to operate portend a higher degree of distraction.

In addition, the method may include calculating a size of the user-interface elements on the screen, since an application may possibly be displayed on various screen sizes, and therefore the degree of distraction may also depend on the size of the screen.

Moreover, the method may include determining a maximum number of user-interface elements. For instance, the information with regard to user-interface elements may reveal that in many cases, fewer user-interface elements, and in other cases, more user-interface elements are displayed. For example, the maximum number of user-interface elements may then be used for the decision.

In addition to or as an alternative to information with regard to the degree of distraction of the application, the provision of information regarding a degree of distraction may also include the acquisition of information concerning a degree of distraction of a driver of the vehicle on the basis of sensor information, e.g., on the basis of pictures from a camera or on the basis of information of operating elements of the vehicle. By evaluating the sensor information, movement patterns of the driver may be determined, for instance, which indicate a distraction.

The provision of data for the display of an application and/or the provision of information with regard to the degree of distraction may include transmission of the data by a server to a client, the client including the screen. For instance, the decision may then be made in the client. However, a decision on the part of the server is also possible.

In many example embodiments, the provision of information regarding the degree of distraction and the display of the application as a function of the information are only carried out if the application is an application foreign to the vehicle, that is, an application not permanently provided in the vehicle. For instance, such applications foreign to the vehicle may be transmitted by a server foreign to the vehicle, e.g., a mobile telephone, to the client including the screen.

In so doing, data for the display of the application on the screen may be transmitted, in particular, according to the Terminal Mode Standard.

In addition, the display may be implemented as a function of a position of the screen in a vehicle. For example, screens to which a driver has access are more critical than screens which are available only to rear-seat occupants, for instance.

In particular, the driving situation may be moving of the vehicle or standing of the vehicle and/or a state of an ignition of the vehicle. The speed of the vehicle or a use of driver assistants may also be taken into account.

Corresponding devices, particularly corresponding clients and corresponding servers, are likewise provided.

Example embodiments of the present invention are explained in greater detail below with reference to the appended Figures.

DETAILED DESCRIPTION

In the following, exemplary embodiments of the present invention are described in more detail with reference to the attached Figures. It should be noted that these exemplary embodiments serve only as example and are not to be interpreted as restrictive. In particular, the description of an exemplary embodiment having a multitude of features is not to be interpreted to the effect that all these features are necessary, since other exemplary embodiments may have fewer features and/or alternative features. In addition, it should be mentioned that features of different exemplary embodiments may be combined with each other, provided nothing otherwise is indicated.

Figure 1:
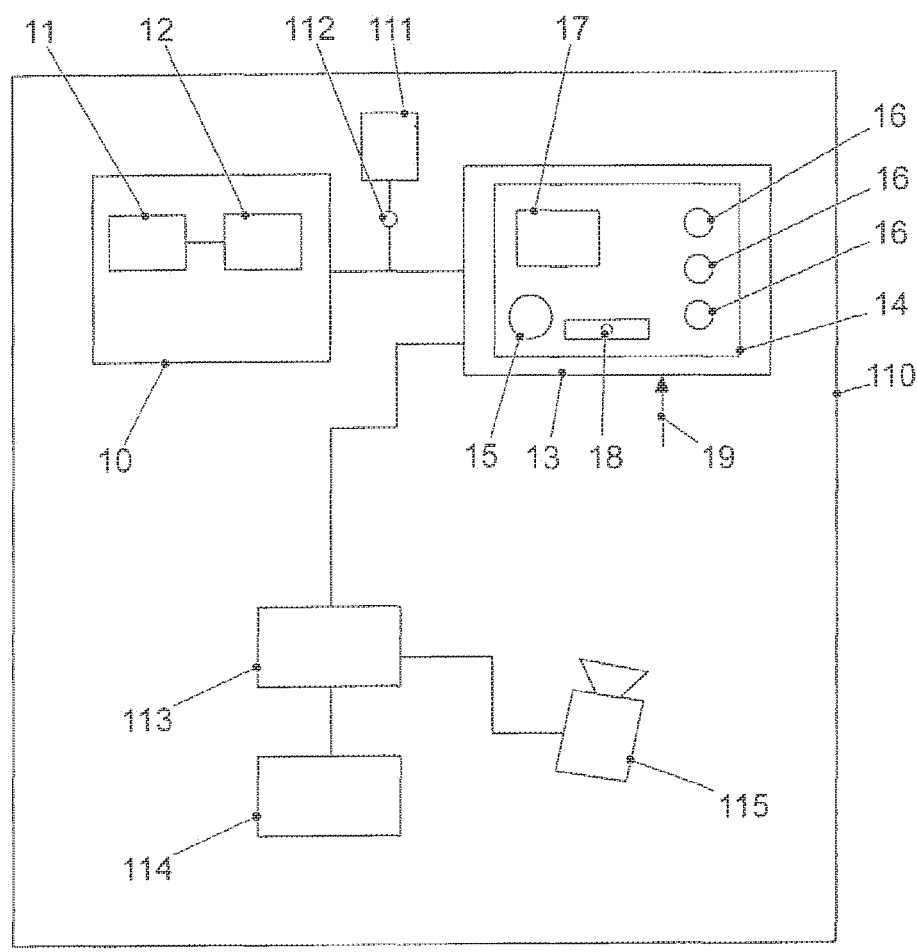
FIG. 1 schematically illustrates a vehicle having a system according to an exemplary embodiment of the present invention.

FIG. 1 schematically illustrates a vehicle 110, e.g., a motor vehicle, which includes a system 10 through 19 according to an example embodiment of the present invention. In the exemplary embodiment illustrated in FIG. 1, the system includes a control device 10 which, as explained in greater detail below, acts as a server, and a multifunctional operating device 13 which acts as a client.

Control device 10 may be equipped to control one or more functions in vehicle 110. Examples for such functions are, for instance, a radio function, an on-board computer, a telephone function, a navigation system, a CD player or a heater of the motor vehicle. In the exemplary embodiment illustrated, control device 10 includes a processor 11 and a memory 12, programs being able to be stored in memory 12 which, when executed on processor 11, implement the control functions of control device 10.

Multifunctional operating device 13 includes a screen 14 which, in the exemplary embodiment illustrated, is a touch-sensitive screen referred to as a touchscreen.

For the operative control of control functions of control device 10 by a user, e.g., a driver of vehicle 110, data for the display of a corresponding application, particularly an operator interface for the application, is transmitted by control device 10 to screen 14. As example, a control knob 15 which, for example, may be operated by a circular movement of a finger on the screen, various buttons 16, a display area 17 for the display of data and a slide control 18 are illustrated on screen 14 in FIG. 1. One or more of the control functions of control device 10 may be operated by a user using these operating elements. In this context, both a combined representation of several control functions, i.e., operating elements for different control functions, in a single display, as well as a change of the representation between different control functions are possible. Besides the user-interface elements shown on screen 14, further "hardware" user-interface elements such as buttons or control knobs may also be made available in multifunctional operating device 13.

For example, the transmission between control device 10 acting as server and multifunctional operating device 13 acting as terminal may be carried out according to the Terminal Mode Standard. The transmission may also take place via a video interface and/or a data interface.

Additionally or as an alternative to the data which multifunctional operating device 14 receives from control device 10, multifunctional operating device 13 may also receive data for the display of an application from a mobile device 111, e.g., a mobile telephone, which is able to be coupled to multifunctional operating device 13 via an interface 112. In particular, modern mobile telephones, what are termed smart phones, are able to display a multitude of applications which may also be games or videos, for example. The data from mobile device 111 may also be transmitted to multifunctional operating device 13 according to the Terminal Mode Standard, for instance.

In exemplary embodiments, mobile device 111 may also transmit data for display on multifunctional operating device 14 to control device 10 according to the Terminal Mode Standard, for example, and control device 10, as a function of this data, may then drive multifunctional operating device 13, using the video interface and/or data interface already mentioned, for instance, for the display of a corresponding application.

Together with the data for the display of the application, in the exemplary embodiment illustrated in FIG. 1, control device 10 and/or mobile device 111 transmit(s) information which identifies a degree of distraction of the application, to multifunctional operating device 13. As a function of this information and a driving situation which the multifunctional operating device receives, as indicated by an arrow 19, multifunctional operating device 13 decides about the display of the application, e.g., whether the application, in this case, the operator interface, will be displayed on the screen. For instance, the driving situation may describe whether the vehicle is stationary or is moving, e.g., by receiving a signal from a speedometer of the vehicle. In exemplary embodiments, a corresponding signal may also be delivered via control device 10. For instance, an operator interface whose degree of distraction exceeds a predefined threshold value may no longer be displayed if the vehicle is moving, while such an operator interface or application is displayed if a vehicle is stationary. A further example for a driving situation is the ignition being on or off, so that it may be determined that the vehicle is not only stationary, but is also switched off.

In particular, the information regarding the degree of distraction may include information about the user-interface elements to be displayed on the screen such as elements 15 through 18, i.e., operating elements and elements conveying information. Such user-interface elements are also referred to as GUI (General User Interface) elements. In particular, which user-interface elements are to be displayed and what size they are may be indicated in the information regarding the degree of distraction. To that end, control device 10 and/or multifunctional operating device 13 may determine the actual displayed size of the user-interface elements as a function of a size of screen 14. For example, many user-interface elements and/or small user-interface elements indicate a high degree of distraction, while few user-interface elements and/or large user-interface elements point to a low degree of distraction.

Thus, for example, the number of user-interface elements or the size of the user-interface elements may be compared to a specific predefined threshold value; this threshold value may be a function of the driving situation.

It should be mentioned that the threshold values above or the decision as to whether the display is implemented may also depend on the placement of multifunctional operating device 13 in vehicle 110. For example, a multifunctional operating device which is positioned such that it can only be operated by a front-seat passenger or even only by rear-seat occupants of a motor vehicle is less critical than a multifunctional operating device which is positioned for operative control by a driver.

It should also be noted that in the case of many exemplary embodiments, the transmission of information which indicates a degree of distraction of the application, and the corresponding evaluation of this information are carried out only for mobile device 111, but not for control device 10. In the case of such exemplary embodiments, it is assumed that only a vehicle's own applications, which are provided especially for use in a vehicle and therefore generally feature only a relatively small degree of distraction, come to be displayed by control device 10, which is installed permanently in the vehicle. In contrast, applications which come from mobile device 111 are applications foreign to the vehicle over which the vehicle manufacturer has no control, for example, and which, at least in many cases, are not provided for use in a vehicle, especially in a moving vehicle, and which therefore show a tendency to a higher degree of distraction. It is also possible to carry out the procedure described above both for control device 10 and for mobile device 111.

In addition, it should be mentioned that in the case of many exemplary embodiments, not all applications running on multifunctional operating device 13 must come from a server such as control device 10 or mobile device 111, but rather may also be permanently installed on the multifunctional operating device. For example, basic functions of the vehicle such as radio or air conditioner may be operable using such permanently installed applications. In the case of many exemplary embodiments, no check is carried out for such applications either. Applications for the operative control of such basic vehicle functions may likewise be transmitted by control device 10.

It should also be mentioned that in the case of many exemplary embodiments, if the degree of distraction of the application exceeds a predefined threshold value, an operator may be asked whether the application should be displayed. The user, e.g., the driver of the vehicle, may then decide, as it were, to allow the application to run at his/her own risk. However, it should be observed that this is optional, and in the case of other exemplary embodiments, for safety reasons, an application whose degree of distraction exceeds a threshold value predefined, for example, as a function of a driving situation, is not displayed as a general principle.

If, on the basis of its degree of distraction, an application is not displayed, in the case of many applications, an alternative application, e.g., a vehicle's own application such as a radio application, may be displayed.

In the following, a few examples for information about user-interface elements which may represent information with regard to the degree of distraction of the application are explained. For example, in many applications, a so-called menu may be displayed on the screen. Such a menu may be displayed in display area 17, for instance, and/or include several buttons such as buttons 16. In this case, the information regarding the user-interface elements may include a (maximum) number of menu levels, a maximum number of visible elements and/or a maximum number of interactive elements such as buttons or input fields; for example, the aforesaid information may be conveyed in the form of integer numerical values. The greater these numbers, the higher the degree of distraction may be rated. Furthermore, information may be sent which indicates whether interactive elements are highlighted by color or three-dimensional display, for example, whether in the case of interactive elements, an audio feedback, i.e., an acoustical return signal is implemented when the element is operated, and/or whether in the case of various ways of operating, different actions are able to be triggered using one interactive element, for example, by pressing the same control button briefly or for a long time. This information may be conveyed as yes/no values. Highlighting interactive elements and an acoustical feedback facilitate the operative control and therefore reduce the degree of distraction, while interactive elements which are operable in varied manner may increase the degree of distraction.

The user-interface elements may also contain text, in which case, information regarding the text may be conveyed. For instance, it may be conveyed whether animated text is used (e.g., in the form of a yes/no value), for example, blinking alphabetic characters, the number of different text sizes in a menu and/or on a screen may be conveyed, e.g., as an integer value; it may be conveyed whether highlighted text is used (e.g., as yes/no value); it may be conveyed whether running text, i.e., text moving through a window, is used (as yes/no value), and in this case, additionally as an option, it may be indicated as an integer value, for example, how long it takes until the text has completely run through. The use of animated text, of different text sizes in a menu, the use of running text, especially if it takes longer until the text has run through, may increase the degree of distraction. The use of highlighted text may at least sometimes reduce the degree of distraction, since it is then easier to recognize important passages.

In addition, it may be indicated in the form of a yes/no value, whether a text input is needed, which may increase the degree of distraction. If this is the case, it may be indicated, for example, whether help is available for the text input, e.g., a phonetic alphabet program or a voice input, which may reduce the degree of distraction. Finally, the total number of alphabetic characters displayed or the maximum number of alphabetic characters displayed for an application on the screen may be indicated, in doing which, a higher number of alphabetic characters may be associated with a higher degree of distraction since, for example, it may take longer to read the entire text.

With respect to the alphabetic characters used in such texts, a minimum height and/or a minimum width may be indicated, in each case as an integer value; as mentioned above, for example, the height and width may be calculated as a function of the size and/or resolution of the screen, e.g., by the respective server, in the case of FIG. 1, by control device 10. In general, greater values signify easier readability and therefore a lower degree of distraction. In addition, it may be conveyed in the form of a yes/no value, for example, whether optimized type sizes may be used, e.g., by utilizing scalable fonts, which may facilitate readability and therefore may reduce the degree of distraction.

Likewise, in many exemplary embodiments, images may be displayed on the screen of the multifunctional operating device. In this case, the maximum number of images displayed, the minimum height of the smallest image, for example, and the minimum width of the smallest image, for example, may be conveyed as information, in doing which, this information may in each instance be conveyed as integer values. As explained above for the alphabetic-character sizes, height and width may be ascertained as a function of a screen size and screen resolution. A higher number of images or smaller images may be associated with a higher degree of distraction.

The information about user-interface elements may also include information about lists to be displayed. For example, such lists may be used when a user selects one or more elements from a plurality of elements. In particular, different yes/no information may be conveyed which indicates the availability of various possibilities for the operative control of such lists.

For example, it may be indicated whether a list may be scrolled by pressing the screen a long time at suitable locations, whether it is possible to change the scroll speed by long pressing and/or by sliding along with the finger, or whether what is referred to as a scrollbar is available. Such elements may simplify the operative control. In addition, it may be indicated whether swiveling of the list is available, e.g., with the aid of arrows, whether the use of a cursor is supported, that is, a marking for the input of text, whether buttons are used in the list and/or whether it is necessary to scroll the list in order to reach such buttons. As a rule, the use of buttons as well as scrolling to reach such buttons makes the operative control of a list more difficult and may therefore increase the degree of distraction.

Information with respect to buttons used may also be conveyed as an example for information regarding user-interface elements. For example, links, e.g., in the case of the display of Internet pages, may also be counted among such buttons, since upon pressing on such a link, an action, e.g., the display of a corresponding new page, is triggered.

For example, a minimum height and a minimum width of buttons used may be transmitted; as already explained above for characters or images, the minimum height and minimum width may be calculated as a function of a screen size and/or screen resolution. Larger buttons simplify the operative control and correspond to a lower degree of distraction accordingly.

In addition, a distance between two interactive areas on the screen may be passed on as an integer value, this distance in turn being able to be calculated as a function of the screen size. Furthermore, the principle according to which buttons operate may be indicated, for example, whether an action is triggered by pressing the button, an action is triggered by releasing a button, or both. Finally, the number of toggle buttons on a screen of an application may be forwarded as integer value; in general, a higher number of buttons may make the operative control more difficult, and thus is associated with a greater degree of distraction.

Furthermore, it may be passed on as a yes/no value, whether slide controls such as slide control 18 in FIG. 1 are used. In the same manner, it may be forwarded as a yes/no value, whether progress bars are used in the case of activities taking a long time; such a progress bar may represent a distraction. The use of pictograms, referred to as icons, may also be characterized by one or more variables. For example, the number of such pictograms, the minimum height of pictograms used or the minimum width of pictograms used, may in each case be transmitted as an integer value, in so doing, the minimum height and the minimum width may each be passed on as an integer value. As explained above, height and width may in turn be calculated as a function of the screen size and/or screen resolution.

In addition, it may be passed on in the form of a yes/no value, whether a specific application supports a special service mode for vehicles, e.g., a service mode in which the operative control is simplified.

A time, e.g., in milliseconds, between the beginning of an interaction and the receipt of a visual or acoustical return signal may likewise be forwarded; a higher value may increase the degree of distraction. Furthermore, it may be transmitted in the form of a yes/no value, whether a specific application uses content from the Internet, especially from the World Wide Web, which in particular, is outside of the control of the application. The use of such elements may increase the degree of distraction.

Finally, it may be indicated in the form of a yes/no value, whether non-standard user-interface elements, referred to as soft DDS, for example, are used. The use of such non-standardized elements may likewise increase the degree of distraction.

The examples above for information with regard to user-interface elements may be used individually or together in different exemplary embodiments. In the case of other exemplary embodiments, on the basis of the user-interface elements employed, for example, a single value which identifies the degree of distraction may be provided, e.g., by a manufacturer of an application, and utilized.

In exemplary embodiments, information with regard to a degree of distraction may already be information as to whether an application may be displayed in a specific driving situation. For instance, such information may include a certification of a specific application, the certification being provided by a certified authority which certifies with a corresponding certificate, for example, that the application is allowed to be displayed in a specific driving situation. Upon an intended start of the application, for instance, by a user input, in the case of many exemplary embodiments, the certificate may then be transmitted to multifunctional operating device 14 and/or control device 10 (if the application runs on mobile device 111). In exemplary embodiments, for example, in the case of an application, mobile device 111 itself may check whether the application is certified for a given driving situation, and then merely inform multifunctional operating device 14 and/or control device 10 as to whether the application may be started. Such a certification may also be provided as a function of the vehicle, so that the application may be executed not only as a function of the driving situation, but also depending on the specific type of vehicle. However, such information regarding the compatibility of the application with specific types of vehicles may also be provided independently of a certification.

It should further be noted that the exemplary embodiment illustrated in FIG. 1 is to be understood only as an example, and different variations are possible. For example, more than one control device or various servers may be present which transmit data regarding different applications to multifunctional operating device 13 or to control device 10. On the other hand, several multifunctional operating devices 13 may also be present in vehicle 110, for instance, for different occupants of the vehicle. In this case, as already explained, whether a specific application is displayed in a specific driving situation may depend on the positioning of the multifunctional operating device.

While in the case of the exemplary embodiment illustrated in FIG. 1, the decision as to whether an application, particularly a user interface, is displayed, is made in multifunctional operating device 13, in other exemplary embodiments, this decision may also be made in control device 10, in doing which, the same information, i.e., information regarding the degree of distraction and data about the driving situation may be utilized for that purpose.

Figure 2:
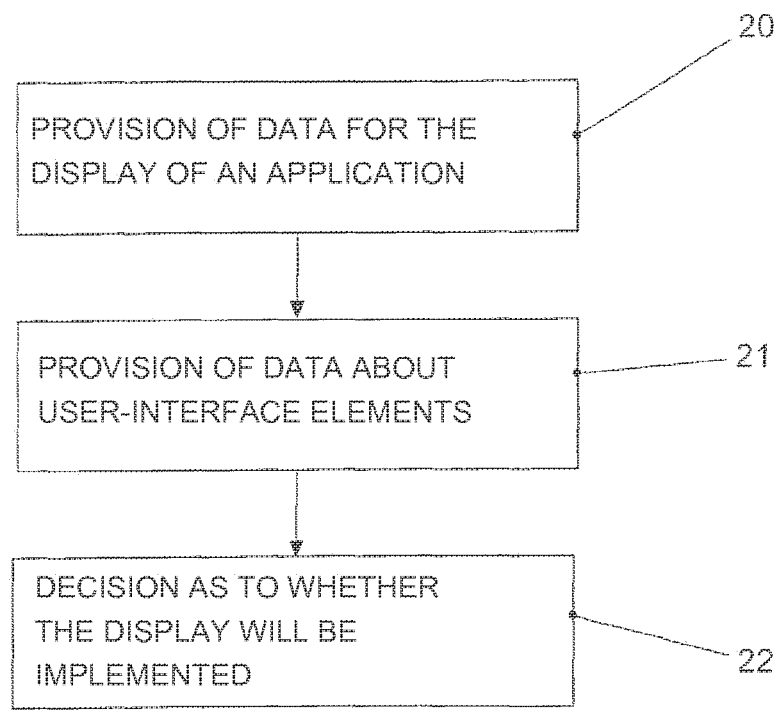
FIG. 2 is a flow chart for illustrating a method according to an exemplary embodiment of the invention.

FIG. 2 shows an exemplary embodiment of a method by which, for example, the functions discussed above may be implemented in the application described with reference to FIG. 1.

In step 20, data for the display of an application is provided, e.g., by control device 10 or mobile device 111, for multifunctional operating device 13.

In step 21, information about user-interface elements or other information regarding a degree of distraction of the application is provided, e.g., likewise by control device 10 of FIG. 1 to multifunctional operating device 13 of FIG. 1.

In step 22, as a function of the information of step 21 and a driving situation, it is decided whether the application will be displayed on a screen.

The variations and modifications discussed with reference to FIG. 1 are likewise applicable to the method illustrated in FIG. 2.

In the exemplary embodiments discussed above, information about the degree of distraction of an application is evaluated in order to decide about the display of the application, especially about whether or not the application will be displayed. In the case of the exemplary embodiment illustrated in FIG. 1, as explained in greater detail hereinafter, in addition, the possibility is provided to determine a degree of distraction of a driver of a vehicle on the basis of sensor data, and to make a decision about the display of the application additionally as a function of the degree of distraction of the driver.

In this context, it should be mentioned that these two possibilities, i.e., decision on the basis of information with regard to the degree of distraction of the application and decision on the basis of information about a degree of distraction of a driver, may not only be implemented together as in the case of the exemplary embodiment illustrated in FIG. 1, but rather that the two possibilities may also be implemented separately from each other. In other words, in many exemplary embodiments, only a decision on the basis of a degree of distraction of the application is used, in many exemplary embodiments, only a decision on the basis of information about a degree of distraction of the driver is used, and in many exemplary embodiments, both are used.

In particular, the device installed in vehicle 110 in FIG. 1 has a camera with which pictures of a driver of the vehicle may be taken. The pictures are supplied to an evaluation device 113. It should be noted that evaluation device 113 may also be integrated in multifunctional operating device 13 or in control device 10, that is, does not have to be a separate element. Additionally or alternatively, signals from various operating elements of vehicle 110 may be supplied to evaluation device 113, corresponding sensors of the operating elements being symbolized by one element 114. For example, data from a steering-angle sensor or data from sensors which evaluate pedal positions of the accelerator or of the brake pedal, for instance, may be provided by sensors 114.

Evaluation device 113 evaluates signals from camera 115 and/or from sensors 114 in order to obtain information regarding a degree of distraction of a driver of vehicle 110.

In this context, camera 115 may be a camera which is sensitive to visible light, but may also be an infrared camera. For example, camera 115 may be mounted on a steering column of vehicle 110 or on an inside roof lining of vehicle 110. In general, however, any positioning of camera 115 is possible, so long as the driver of vehicle 110 is able to be captured.

For instance, evaluation device 113 may evaluate pictures from the camera in order to check whether and for what portion of time the eye of the driver is directed toward the road. It may also be analyzed, how frequently the driver directs his eyes away from the road. The less the eye is directed toward the road, the higher the degree of distraction of the driver may be graded. In particular, it may also be determined whether the eye of the driver, and therefore the attention of the driver, is directed toward screen 14.

In addition or alternatively, evaluation device 113 may evaluate information from sensors 114 to thus analyze a driving behavior of the driver, e.g., his/her steering behavior, behavior in operating the pedals or perhaps a velocity behavior. For example, more frequent jerky steering-wheel motions may point to a high degree of distraction.

Similarly as above for the information with regard to the degree of distraction of the application, a decision may then also be made about the display of the application on the basis of the information about the degree of distraction of the driver, and in particular, the application may not be displayed or a display of the application may be ended if the degree of distraction of the driver exceeds a predefined threshold value. Optionally, a warning may also be output, for example, on screen 14, and/or it may be queried via screen 14, for instance, whether the application should continue to be displayed, so that the driver can then decide to allow the application to keep running on his/her own responsibility.

Similar to the evaluation of the degree of distraction of the application, the device illustrated in FIG. 1 may also be configured such that evaluation device 113 is only activated when an application foreign to the vehicle, e.g., an application supplied by mobile device 111, is displayed or should be displayed on screen 14, and/or when the driver of the vehicle interacts with multifunctional operating device 13. Upon detection of a distraction, a switchover may then be made to a vehicle's own application, for instance.

Figure 3:
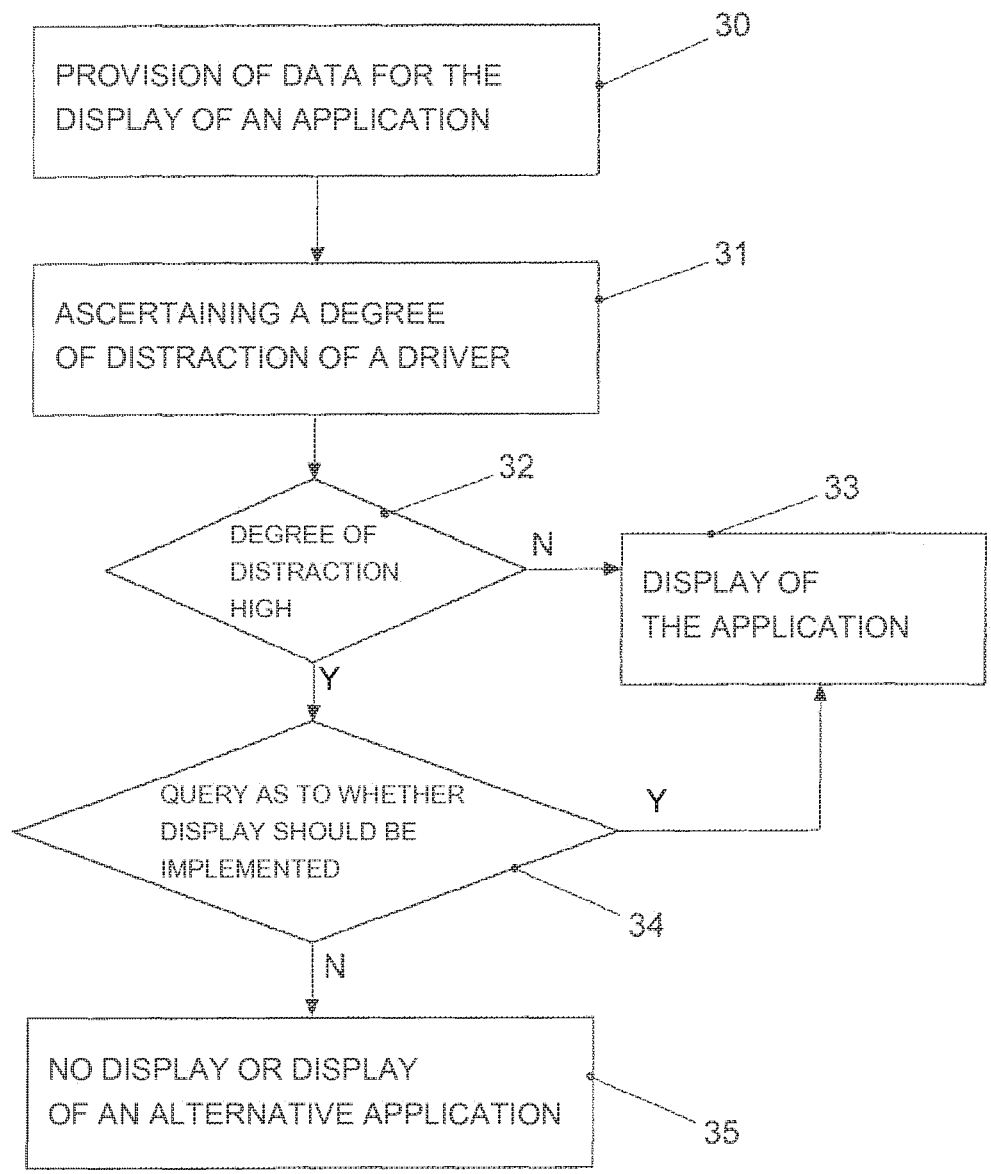
FIG. 3 is a flow chart for illustrating a method according to a further exemplary embodiment of the present invention.

In FIG. 3, an exemplary embodiment of a method is illustrated which represents an example for the evaluation of a degree of distraction of a driver explained above, and which may be implemented in the device of FIG. 1, for instance, but is also usable independently of it.

In step 30, data is provided, e.g., by control device 10 of FIG. 1 or by mobile device of FIG. 1, for the display of an application.

In step 31, a degree of distraction of a driver of a vehicle is ascertained, e.g., by evaluation device 113 of FIG. 1.

In step 32, it is checked whether the degree of distraction of the driver is high, for example, exceeds a predefined threshold value. If no, in step 33, the application is displayed normally or the application continues to be displayed. If the degree of distraction is high, in step 34, it is queried whether the application should be displayed, that is, the driver of the vehicle is asked to confirm the display. If it is confirmed that the application should be displayed, in step 33, the application is in turn displayed. If no, in step 35, the application is not displayed, and optionally, an alternative application is displayed.

In view of the variations and modifications discussed, it should be appreciated that a multitude of variations is possible, and therefore the scope hereof is not limited to the exemplary embodiments presented.

The invention claimed is:

1. A method for displaying an application in a vehicle, comprising:
providing data for displaying an application on a screen;
defining a threshold distraction value as a function of a driving situation of the vehicle;
providing information relating to a degree of application distraction based on user-interface elements of the application;
determining the degree of application distraction based on the provided information relating to the degree of application distraction, wherein the degree of application distraction is increased by applications requiring text input, and wherein the degree of application distraction is decreased by at least one of applications including highlighting of interactive elements or text, acoustical feedback, phonetic alphabet text input, and/ or voice input;
wherein driver interaction with the application causes the degree of application distraction to be determined;
comparing the determined degree of application distraction to the threshold distraction value; and
if the determined degree of application distraction is less than the threshold distraction value, displaying the application on the screen, and if the determined degree of application distraction is more than the threshold distraction value, preventing the display of the application on the screen.

2. The method according to claim 1, wherein the information relating to the degree of application distraction includes information about a user-interface of the application.

3. The method according to claim 2, further comprising calculating a size of user-interface elements as a function of a size and/or a resolution of the screen, the size of the user-interface elements indicating the degree of application distraction.

4. The method according to claim 2, wherein the displaying is implemented as a function of a size of user-interface elements, a number of user-interface elements, and/or a form of user-interface elements.

5. The method according to claim 1, wherein the providing of the information relating to the degree of application distraction includes transmitting the information by a server to a client including the screen.

6. The method according to claim 1, wherein the information relating to a degree of application distraction includes a certificate of the application or information derived from the certificate.

7. The method according to claim 1, wherein the driving situation includes a moving vehicle, a stationary vehicle, a vehicle with ignition switched off, and/or a vehicle with ignition switched on.

8. The method according to claim 1, wherein the providing of data for the display of an application includes transmitting the data by a server to a client including the screen.

9. The method according to claim 1, wherein the providing of information and the display as a function of the information are only carried out when the application is an application foreign to the vehicle.

10. The method according to claim 9, wherein the providing of data for the display of an application includes transmitting the data by a server to a client including the screen, and wherein it is determined that an application is an application foreign to the vehicle if the server is a server foreign to the vehicle.

11. The method according to claim 1, wherein the display is implemented as a function of a position of the screen in the vehicle.

12. The method according to claim 1, wherein the display is implemented as a function of a type of the vehicle.

13. The method according to claim 1, wherein the displaying of the application on the screen includes displaying a warning as a function of the information relating to the degree of application distraction.

14. The method according to claim 1, wherein the displaying of the application as a function of the information relating to the degree of application distraction includes querying to a user as to whether the application should be displayed, as a function of the degree of application distraction.

15. The method according to claim 1, wherein if the degree of application distraction exceeds a first threshold value, displaying a warning on the screen, and if the degree of application distraction exceeds a second threshold value, restricting the display of the application.

16. A device, comprising:
a screen; and
an operating device adapted to receive data for displaying an application on the screen, to define a threshold distraction value as a function of a driving situation of the vehicle, to receive information relating to a degree of application distraction based on user-interface elements of the application, to determine the degree of application distraction based on the provided information relating to the degree of application distraction, wherein the degree of application distraction is increased by applications requiring text input, and wherein the degree of application distraction is decreased by at least one of applications including highlighting of interactive elements or text, acoustical feedback, phonetic alphabet text input, and/or voice input, to compare the determined degree of application distraction to the threshold distraction value, wherein driver interaction with the application causes the degree of application distraction to be determined; and, if the determined degree of application distraction is less than the threshold distraction value, to display the application on the screen, and if the determined degree of application distraction is more than the threshold distraction value, to prevent the display of the application on the screen.

17. The device according to claim 16, further comprising a controller adapted to transmit the data for the display of the application and/or to transmit the information relating to the degree of application distraction.

18. The device according to claim 16, wherein the device is adapted to perform a method for displaying the application in a vehicle, the method including:
  providing the data for displaying the application on the screen;
  providing the information relating to the degree of application distraction; and
  displaying the application on the screen as a function of the information relating to the degree of application distraction and the driving situation of the vehicle.

19. A device, comprising:
  a controller adapted to transmit data to display an application on a screen of a client;
  an evaluator adapted to evaluate information relating to a degree of distraction, wherein the evaluating includes determining (a) a degree of application distraction representing a degree to which the application is distracting based on user-interface elements of the application, wherein the degree of application distraction is increased by applications requiring text input, and wherein the degree of application distraction is decreased by at least one of applications including highlighting of interactive elements or text, acoustical feedback, phonetic alphabet text input, and/or voice input, and (b) a degree of driver distraction representing a degree to which the driver is distracted on the basis of at least one of a camera monitoring the direction of the driver's vision, a steering angle sensor, and/or a pedal position sensor; and
  a processor adapted to decide about the display of the application on the screen as a function of the information relating to the degree of distraction and a driving situation;
  wherein the evaluator is adapted to determine the degree of distraction in response to driver interaction with the application.

20. The device according to claim 19, wherein the device is adapted to perform a method for displaying the application in a vehicle, the method including:
  providing the data for displaying the application on the screen;
  providing the information relating to the degree of distraction; and
  displaying the application on the screen as a function of the information relating to the degree of distraction and the driving situation of the vehicle.

21. The device according to claim 19, wherein the degree of driver distraction is determined when the application is foreign to the vehicle.

22. A method for displaying an application in a vehicle, comprising:
  providing data for displaying an application on a screen;
  defining a threshold distraction value;
  providing information relating to a degree of driver distraction on the basis of at least one of a camera monitoring the direction of the driver's vision, a steering angle sensor, and/or a pedal position sensor;
  determining the degree of driver distraction based on the provided information relating to the degree of driver distraction;
  comparing the determined degree of driver distraction to the threshold distraction value; and
  if the determined degree of driver distraction is less than the threshold distraction value, displaying the application on the screen, and if the determined degree of driver distraction is more than the threshold distraction value, preventing the display of the application on the screen;
  wherein driver interaction with the application causes the degree of driver distraction to be determined.

23. The method according to claim 22, wherein the sensor information includes information from picture data of a camera and/or information of operating elements of the vehicle.

24. The method according to claim 22, wherein the degree of driver distraction is determined when the application is foreign to the vehicle.

* * * * *